Figure 1:
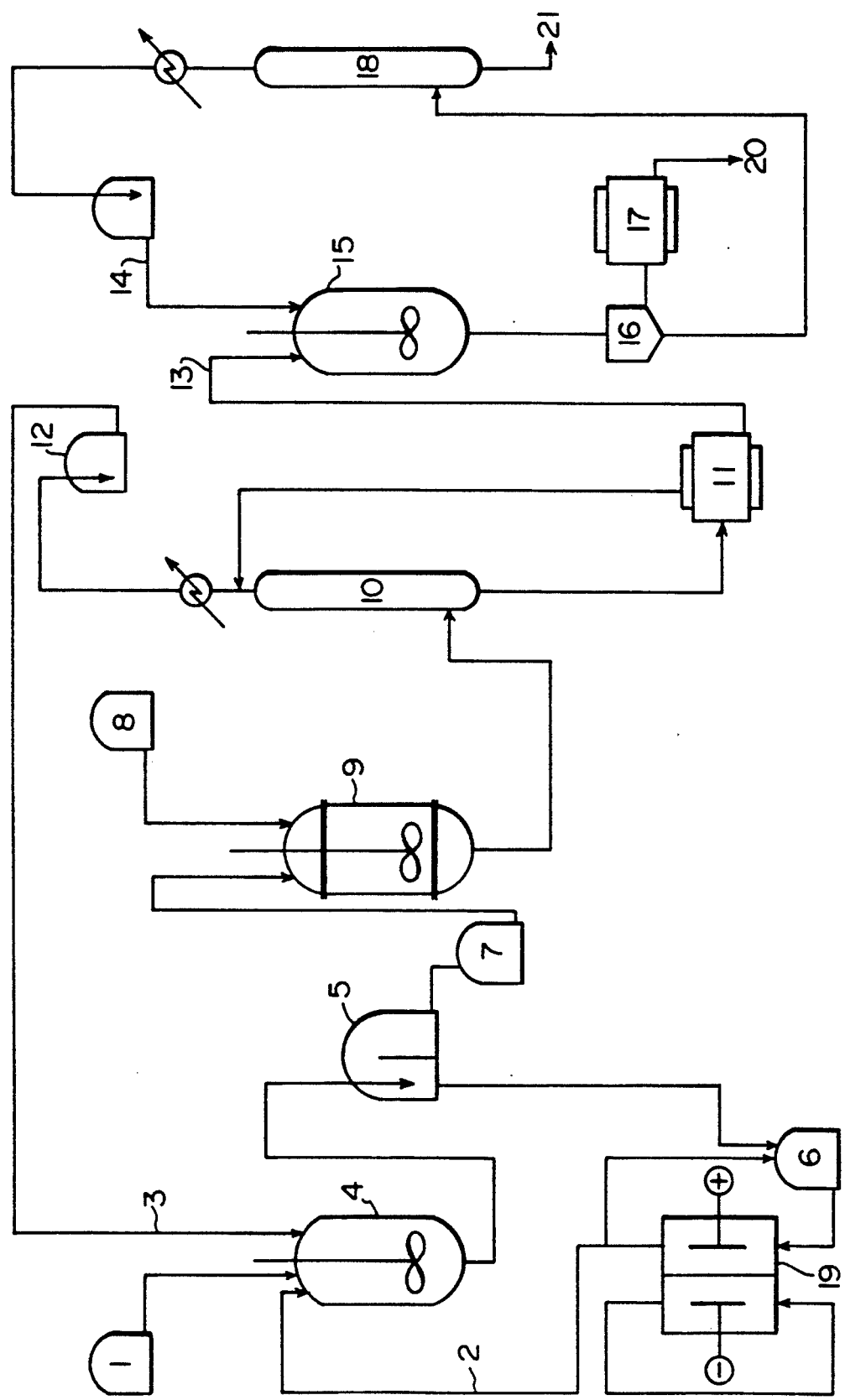

United States Patent [19]

Sugishima et al.

[11] Patent Number: 5,329,026
[45] Date of Patent: Jul. 12, 1994

[54] PROCESS FOR PREPARATION OF 2-SUBSTITUTED 1,4-NAPHTHOQUINONE

[75] Inventors: Noboru Sugishima; Noriaki Ikeda; Yasushi Fujii, all of Himeji; Ryuji Aoki, Hyogo; Yumi Hatta, Himeji, all of Japan

[73] Assignee: Nippon Shokubai Kagaku Kogyo Co., Ltd., Tokyo, Japan

[21] Appl. No.: 618,941

[22] Filed: Nov. 28, 1990

[30] Foreign Application Priority Data

Nov. 28, 1989 [JP] Japan ................... 1-306660
Feb. 28, 1990 [JP] Japan ................... 2-45530

[51] Int. Cl.$^5$ ............................................. C07C 50/18
[52] U.S. Cl. ................................. 552/208; 552/292
[58] Field of Search ............................. 552/292, 208

[56] References Cited

U.S. PATENT DOCUMENTS 3,953,482  4/1976  Sugano et al. ................ 552/208
4,632,782  12/1986  Komatsu et al. ............... 552/292
4,639,298  1/1989  Kreh et al. ................... 552/292

OTHER PUBLICATIONS

Patent Abstracts of Japan, vol. 10, No. 128 (C-345) (2185) 1986.
Chemical Abstracts, vol. 110, 1989, Abstract No. 23577.

Primary Examiner—C. Warren Ivy
Assistant Examiner—Raymond Covington
Attorney, Agent, or Firm—Sherman and Shalloway

[57] ABSTRACT

A process for preparation of a 2-substituted-1,4-naphthoquinone which comprises oxidizing a 2-substituted naphthalene to obtain reaction products comprising a 2-substituted-1,4-naphthoquinone and a 6-substituted-1,4-naphthoquinone; adding a diene compound to the reaction products and heating the mixture to form a Diels-Alder reaction adduct between the diene compound and the 6-substituted-1,4-naphthoquinone in the reaction products; and separating the 2-substituted-1,4-naphthoquinone from the adduct.

13 Claims, 3 Drawing Sheets

PROCESS FOR PREPARATION OF 2-SUBSTITUTED 1,4-NAPHTHOQUINONE

This invention relates to a process for industrially preparing a 2-substituted-1,4-naphthoquinone by oxidation of a 2-substituted naphthalene. More detailedly, this invention relates to a process for preparation of a 2-substituted-1,4-naphthoquinone of a high purity by separating and removing a 6-substituted-1,4-naphthoquinone from a mixture of the 2-substituted-1,4-naphthoquinone and the 6-substituted-1,4-naphthoquinone obtained by oxidation of a 2-substituted naphthalene. Among 2-substituted-1,4-naphthoquinones, 2-methyl-1,4-naphthoquinone is also called menadione or vitamin $K_3$, is a kind of vitamins having a blood-coagulating action, and is a useful drug as a pharmaceutical for the human body or an additive for livestock feeds. Further, its hydrogen sulfite salt is water soluble, and useful as a pharmaceutical or a raw material thereof or an additive for feeds.

This invention further relates to a process for obtaining a 5,8-dihydro-2-substituted-1,4-anthraquinone and/or a 2-substituted anthraquinone (hereinafter, both the compounds are generally referred to as 2-substituted anthraquinones) useful as a pulp digestion auxiliary or a raw material of anthraquinone derivatives, from a 6-substituted-1,4-naphthoquinone accessorily produced by oxidation of a 2-substituted naphthalene.

As for preparation processes of 2-substituted-1,4-naphthoquinones, a process has hitherto been carried out which comprises oxidizing a 2-substituted naphthalene with an oxidizing agent such as chromic acid or hydrogen peroxide. However, a 2-substituted-1,4-naphthoquinone produced by such a process is accompanied by a large amount of an accessorily produced 6-substituted-1,4-naphthoquine as an impurity, and it is necessary to separate and remove the latter. Further, the accessorily produced 6-substituted-1,4-naphthoquinone have no use as it is and is usually discarded, and the labor and cost for the treatment cannot be neglected and are a large problem. Further, an indirect electrolytic oxidation reaction has also been carried out which comprises oxidizing a 2-substituted naphthalene with an acidic aqueous solution of a ceric salt, and then electrolytically oxidizing the formed cerous salt to reproduce an acidic aqueous solution of the ceric salt and reuse it. Although this process has advantages that harmful chromium is not used and the selectivity of the 2-substituted-1,4-naphthoquinone is improved, the process still has a drawback of accessory production of a 6-substituted-1,4-naphthoquinone.

The 6-substituted-1,4-naphthoquinone accessorily produced in obtaining a 2-substituted-1,4-naphthoquinone by oxidation of a 2-substituted naphthalene is mutually in the relation of an isomer with the 2-substituted-1,4-naphthoquinone, and separation of these compounds is difficult since they are very much alike in physical properties. For example, as a process for obtaining a high purity 2-methyl-1,4-naphthoquinone from a reaction mixture containing 2-methyl-1,4-naphthoquinone and 6-methyl-1,4-naphthoquinone obtained by oxidation of 2-methylnaphthalene, a process which comprises treating the reaction mixture with an aqueous hydrogen sulfite salt solution (Japanese Laid-Open Patent Publication No. 252,445/1985) was proposed, but this process has many steps and every time each step is completed, yield decreases, and thus overall yield is insufficient.

A 2-substituted naphthalene as a starting material, as long as it is not sufficiently purified, tends to contain other naphthalenes such as a 1-substituted naphthalene and naphthalene. Although these naphthalenes are also converted to the corresponding 1,4-naphthoquinones such as a 5-substituted-1,4-naphthoquinone and 1,4-naphthoquinone by an oxidation reaction, these compounds, like 6-methyl-1,4-naphthoquinone, closely resemble the 2-substituted-1,4-naphthoquinone in physical properties, and are difficult to separate.

An object of the invention is to provide a process for obtaining a 2-substituted-1,4-naphthoquinone of a high purity and, in preparation of the 2-substituted-1,4-naphthoquinone by oxidation of a 2-substituted napthalene, effectively separating and removing the accessorily produced 6-substituted-1,4-naphthoquinone.

Another object of the invention is to economically prepare a 2-substituted-1,4-naphthoquinone by converting the 6-substituted-1,4-naphthoquinone accessorily produced by oxidation of a 2-substituted naphthalene to 2-substituted anthraquinones to utilize them effectively.

The present inventors vigorously studied to discover a process to attain the above objects, and found that when a diene compound is added to the products of a 2-substituted naphthalene oxidation reaction and the mixture is heated, due to the difference of steric hindrance and electron density, the 2-substituted-1,4-naphthoquinone hardly reacts with the diene compound but the 6-substituted-1,4-naphthoquinone readily reacts with the diene compound to form a corresponding Diels-Alder reaction adduct.

Thus, according to this invention is provided a process for preparation of a 2-substituted-1,4-naphthoquinone which comprises oxidizing a 2-substituted naphthalene [which is represented by the general formula (A) in the following reaction formulae] to obtain reaction products comprising a 2'-substituted-1,4-naphthoquinone [which is represented by the general formula (B) in the following reaction formulae] and a 6-substituted-1,4-naphthoquinone [which is represented by the general formula (C) in the following reaction formulae]; adding a diene compound [for example, a 1,3-butadiene represented by the general formula (D) in the following reaction formulae] to the reaction products and heating the mixture to form a Dieis-Alder reaction adduct [which is represented by the general formula (E) in the following reaction formulae]between the diene compound and the 6-substituted-1,4-naphthoquinone in the reaction products; and separating the 2-substituted-1,4-naphthoquinone from the adduct.

Reaction formulae:

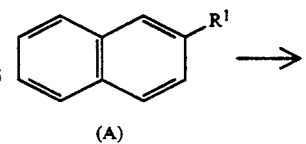

(A)

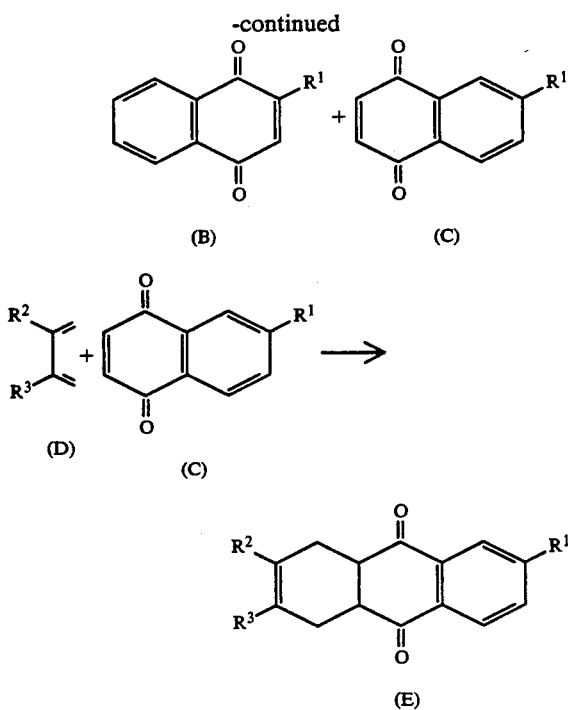

(wherein $R^1$, $R^2$ and $R^3$ and each represent a substituent).

Further, according to this invention, an overall process for preparation of 2-substituted-anthraquinone(s) [a 5,8-dihydro-2-substituted-anthraquinone represented by the general formula (F) and/or a 2-substituted-anthraquinone represented by the general formula (G) in the following reaction formulae] is also provided which comprises oxidizing a Dieis-Alder reaction adduct between a 6-substituted-1,4-naphthoquinone and a diene compound.

Reaction formulae:

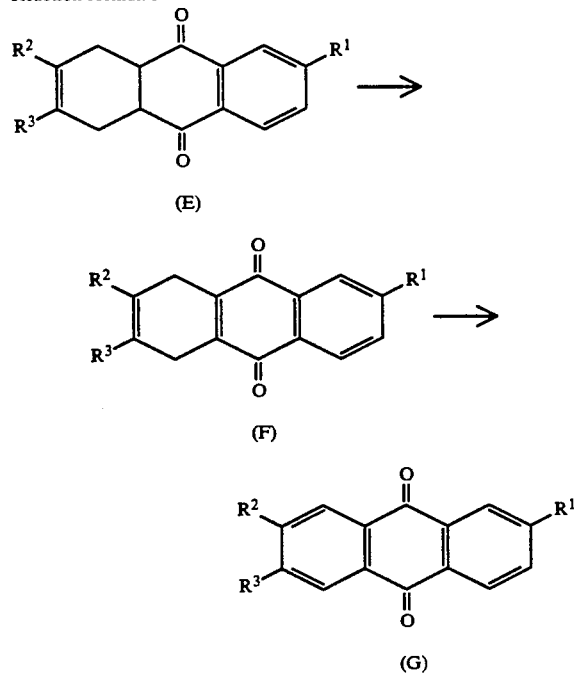

(wherein $R^1$, $R^2$ and $R^3$ are as defined above).

When a starting raw material 2-substituted naphthalene contains other naphthalenes such as a 1-substituted naphthalene and naphthalene, these latter naphthalenes are also converted to the corresponding 1,4-naphthoquinones such as a 5-substituted-1,4-naphthoquinone and 1,4-naphthoquinone by the aforementioned oxidation reaction. These 1,4-naphthoquinones are readily converted to adducts with a diene compound and these adducts are largely different from the 2-substituted-1,4-naphthoquinone in various physical properties, and thus the 2-substituted-1,4-naphthoquinone can readily be separated and purified. Further, these adducts between the 1,4-naphthoquinones and the diene compound, like the adduct represented by the general formula (E), can be separated and oxidized to afford anthraquinones useful as a pulp digestion auxiliary or the like. Although, in the following description, detailed description is not made on the above reaction caused by the 1-substituted naphthalene or naphthalene, or the like, the reaction or the like is as in the case of the 6-substituted-1,4-naphthoquinone. About the case of a 1-substituted naphthalene these series of reaction formulae are shown below:

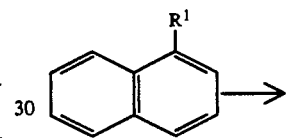

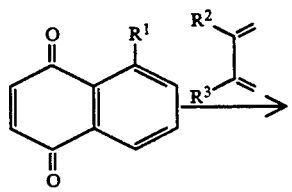

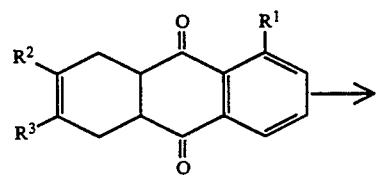

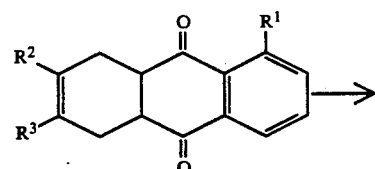

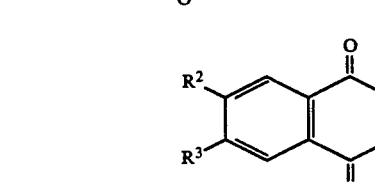

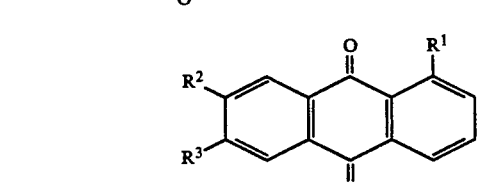

A 2-substituted naphthalene used in the invention is one wherein a substituent is introduced in the 2-position of naphthalene, and examples of the substituent [$R^1$ in the above general formula (A)] include alkyl groups having 1 to 5 carbon atoms, a nitro group, a carboxyl group, a halogen atoms, etc.

The oxidation reaction of a 2-substituted naphthalene can be carried out by a so far known general process as abovementioned. Among them, an indirect electrolytic oxidation reaction wherein a 2-substituted naphthalene is oxidized with an acidic aqueous solution of a ceric salt is a preferred process because harmful chromium is not used and a 2-substituted-1,4-naphthoquinone is formed in a comparatively good selectivity. Examples of the ceric salt constituting the acidic aqueous solution of the ceric salt include ceric salts such as ceric sulfate and ceric nitrate, and examples of the acid include inorganic acids such as sulfuric acid and nitric acid and organic acid such as methanesulfonic acid and acetic acid. In general, by an oxidation reaction, a 2-substituted naphthalene is converted to a 2-substituted-1,4-naphthoquinone, but accessory production of a 6-substituted-1,4-naphthoquinone is not avoidable.

Then, the 6-substituted-1,4-naphthoquinone in the reaction products by the oxidation reaction is reacted with a diene compound in the presence of a solvent to form a Diels-Alder reaction adduct.

As diene compounds used in the Diels-Alder reaction are preferably used 1,3-butadienes such as butadiene, methylbutadiene, dimethylbutadiene, cyclopentadiene and cyclohexadiene, but other diene compounds may also be used. When a 1,3-butadiene represented by the general formula (D)

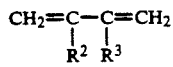

(wherein $R^2$ and $R^3$ are each independently any one of a hydrogen atom, a methyl group and an ethyl group) is used, the Diels-Alder reaction adduct of the formed 6-substituted-1,4-naphthoquinone with the 1,3-butadiene can be separated and oxidized to obtain 2-substituted anthraquinones useful as a pulp digestion auxiliary or a raw material for synthesis of anthraquinone derivatives. Namely, as is preferred, this case leads to the results that a 6-substituted-1,4-naphthoquinone, which has so far been discarded as a by-product, can effectively be utilized and that as a result a 2-substituted-1,4-naphthoquinone can inexpensively be prepared.

Since a too small use amount of the diene compound leads to a slow reaction rate and on the other hand a too large use amount thereof leads to polymerization of the diene compound, etc., the use amount of the diene compound is 1.0 to 2.0 moles, preferably 1.1 to 1.5 moles per mole of the 6-substituted-1,4-naphthoquinone.

As for a solvent used in the Diels-Alder reaction, any solvent can be used so long as the 6-substituted-1,4-naphthoquinone and the diene compound have therein a large solubility, and examples of preferred solvents include aromatic hydrocarbons such as benzene, toluene and xylene; mono-, di- and tri-ethylene glycol monoalkyl ethers such as ethylene glycol monooctyl ether, diethylene glycol monoethyl ether and triethylene glycol monomethyl ether; organic chlorine compounds such as chloroform and carbon tetrachloride; and the like.

As for the concentration of a 6-substituted-1,4-naphthoquinone used in the Diels-Alder reaction, too low a concentration leads to a slow reaction rate and on the other hand too high a concentration causes side reactions such as polymerization. Therefore, the use amount of a solvent used in the Diels-Alder reaction is determined so that the concentration of the 6-substituted-1,4-naphthoquinone becomes preferably 0.5 to 15 weight %, more preferably 1 to 10 weight %. Further, when the Diels-Alder reaction temperature is too high, not only the 6-substituted-1,4-naphthoquinone but also the 2-substituted-1,4-naphthoquinone react with the diene compound and a lower yield is caused, and on the other hand, when the temperature is too low, the reaction time becomes longer and thus an disadvantage on the cost aspect is caused. Therefore, the reaction temperature is preferably 50° to 200° C., more preferably 80° to 150° C. In view of the cost aspect and side reaction, the reaction time is appropriately 2 to 20 hours and preferably 3 to 10 hours.

Further, in the Diels-Alder reaction, it is preferred to use a polymerization inhibitor.

Due to the difference of steric hindrance and electron density, the 2-substituted-1,4-naphthoquinone hardly reacts with the diene compound, whereas the 6-substituted-1,4-naphthoquinone readily reacts with the diene compound to form a Diels-Alder reaction adduct. The adduct is largely different from the 2-substituted-1,4-naphthoquinone in various characteristics, and therefore separation and purification of the 2-substituted-1,4-naphthoquinone become very easy, and for example by simple manipulation(s) such as recrystallization and extraction the 2-substituted-1,4-naphthoquinone of a high purity can be obtained.

When the separation and purification of the 2-substituted-1,4-naphthoquinone are carried out by recrystallization, the solvent is distilled away from the reaction mixture obtained by the Diels-Alder reaction, the 2-substituted-1,4-naphthoquinone is recrystallized using a recrystallization solvent, and the resulting crystals are collected by filtration and dried to obtain the 2-substituted-1,4-naphthoquinone of a high purity. As the recrystallization solvent, such a solvent is suitable if there is a difference between the solubilities of the 2-substituted-1,4-naphthoquinone and the adduct therein, and preferred are alcohols such as methanol, ethanol, propanol and butanol.

Further, when, for example, a hydrogensulfite salt is added to the reaction mixture after the Diels-Alder reaction, the 2-substituted-1,4-naphthoquinone is extracted into the aqueous phase as its hydrogensulfite salt, and the adduct remains in the oil phase (the phase of the solvent used in the Diels-Alder reaction). The aqueous phase is taken out and subjected to recrystallization with addition of a recrystallization solvent or to salting out to deposit the 2-substituted1,4-naphthoquinone hydrogensulfite salt, which is then filtered and dried to obtain the 2-substituted-1,4-naphthoquinone of a high purity.

The appended drawings are flow sheet charts describing the steps in the preferred embodiments of the invention.

FIG. 1 describes an overall preparation process of a 2-substituted-1,4-naphthoquinone of a high purity using a 2-substituted naphthalene as a starting raw material. Although in the drawing an indirect electrolytic oxidation reaction using an acidic aqueous solution of a ceric salt is exemplified as the 1st step (oxidation reaction), this 1st step can be replaced by another oxidation reaction such as a method using an oxidizing agent such as chromic acid or hydrogen peroxide.

The acidic aqueous solution of the cerium salt is supplied to an electrolytic vessel 19 from a tank 6 and electorolytically oxidized therein, and the resulting acidic aqueous solution of the ceric salt is supplied to an oxidation and extraction vessel 4. On the other hand, a starting raw material 2-substituted naphthalene is supplied to the oxidation and extraction vessel 4 from a tank 1, and the mixture is warmed to a predetermined temperature with stirring to carry out an oxidation reaction (The 1st step). By the oxidation reaction of the 1st step, the 2-substituted naphthalene is converted to the corresponding 2-substituted-1,4-naphthoquinone, but the corresponding 6-substituted-1,4-naphthoquinone is accessorily produced. On the other hand, the ceric salt consumed as an oxidizing agent is reduced to the corresponding cerous salt.

After the oxidation reaction of the 1st step, a solvent is supplied to the oxidation and extraction vessel 4 from a tank 12, whereby the oxidation reaction products comprising the 2-substituted-1,4-naphthoquinone and the 6-substituted-1,4-naphthoquinone are extracted into the solvent layer to be separated from the aqueous layer. On the other hand, the cerous salt formed in the 1st step and the unreacted ceric salt are extracted into the aqueous phase. The contents of the oxidation and extraction vessel 4 are taken out, and, after supply to an oil-water separation vessel 5, the solvent phase is transferred to a tank 7 and the aqueous phase containing the cerium salts to the tank 6 (the 2nd step).

The solvent used therein is preferably one mentioned above as a solvent used in the Diels-Alder reaction so that it may be used as it is as the solvent in the 3rd step.

The aqueous phase containing the cerium salts, which was transferred to the tank 6, is transferred to the electrolytic vessel 19, where the cerous salt in the aqueous phase is electrolytically oxidized to the ceric salt which is then reused as the acidic aqueous solution of the ceric salt.

The solvent phase containing the 2-substituted-1,4-naphthoquinone and the 6-substituted-1,4-naphthoquinone extracted and separated in the 2nd step, and a diene compound are supplied to a Diels-Alder reaction vessel 9 from the tank 7 and a tank 8 respectively to carry out a Diels-Alder reaction (the 3rd step). As aforementioned, the 2-substituted-1,4-naphthoquinone hardly reacts with the diene compound, whereas the 6-substituted-1,4-naphthoquinone readily reacts with the diene compound to form a corresponding adduct.

After the Diels-Alder reaction, the solvent is recovered from the reaction mixture. In case of the flow sheet of FIG. 1, the Diels-Alder reaction mixture is supplied to a distillation tower 10 and distilled, and the solvent is recovered into the tank 12. In this connection, the unreacted 2-substituted naphthalene can also be recovered together with the solvent. The mixture containing the 2-substituted-1,4-naphthoquinone and the adduct of the 6-substituted-1,4-naphthoquinone with the diene compound is taken out from the bottom part of the distillation tower 10 (the 4th step). Then, this mixture is supplied to a vacuum dryer 11, where the remaining solvent is further completely removed.

Finally, the mixture obtained after the removal of the solvent is subjected to a manipulation such as recrystallization or extraction to remove the Diels-Alder reaction adduct between the 6-substituted-1,4-naphthoquinone and the diene compound and thus obtain the 2-substituted-1,4-naphthoquinone of a high purity (the 5th step). That is to say, the mixture, which was taken out from the vacuum dryer 11 and comprises the 2-substituted-1,4-naphthoquinone and the adduct between the 6-substituted-1,4-naphthoquinone and the diene compound, is supplied to a crystallization bath 15, a recrystallization solvent from a recrystallization solvent tank 14 is added to conduct recrystallization, the resulting slurry is filtered by a filter 16, and the crystals are dried by a vacuum dryer 17 to obtain crystals of the 2-substituted-1,4-naphthoquinone of a high purity. On the other hand, the filtrate is supplied to a recrystallization solvent recovery tower 18 to be distilled, and the resulting solvent is recovered into the recrystallization solvent tank 14 and reused.

In case where 2-methyl-1,4-naphthoquinone hydrogensulfite salt, which is useful as an additive (hemostyptic) of feeds and has a high purity, is prepared, it is sufficient that an aqueous hydrogensulfite salt solution is added to a Diels-Alder reaction mixture, which was obtained in the same manner as above and contains a Diels-Alder reaction adduct between 6-methyl-1,4-naphthoquinone and a diene compound, to extract 2-methyl-1,4-naphthoquinone as its hydrogensulfite salt into the aqueous phase. Used as the hydrogensulfite salt is a hydrogensulfite salt of an alkali metal such as sodium or potassium, or a hydrogensulfite of an amine such as dimethylpyridiminol. By adding an aqueous hydrogensulfite salt solution to the Diels-Alder reaction mixture, 2-methyl-1,4-naphthoquinone is converted to its hydrogensulfite salt to be extracted into the aqueous phase from the solvent phase, and thereby separated from the adduct between 6-methyl-1,4-naphthoquinone and the diene compound in the solvent phase. Thereafter, for example, a recrystallization solvent is added to the taken out aqueous phase to deposit 2-methyl-1,4-naphthoquinone hydrogensulfite, which is then taken out as crystals.

Figure 2:
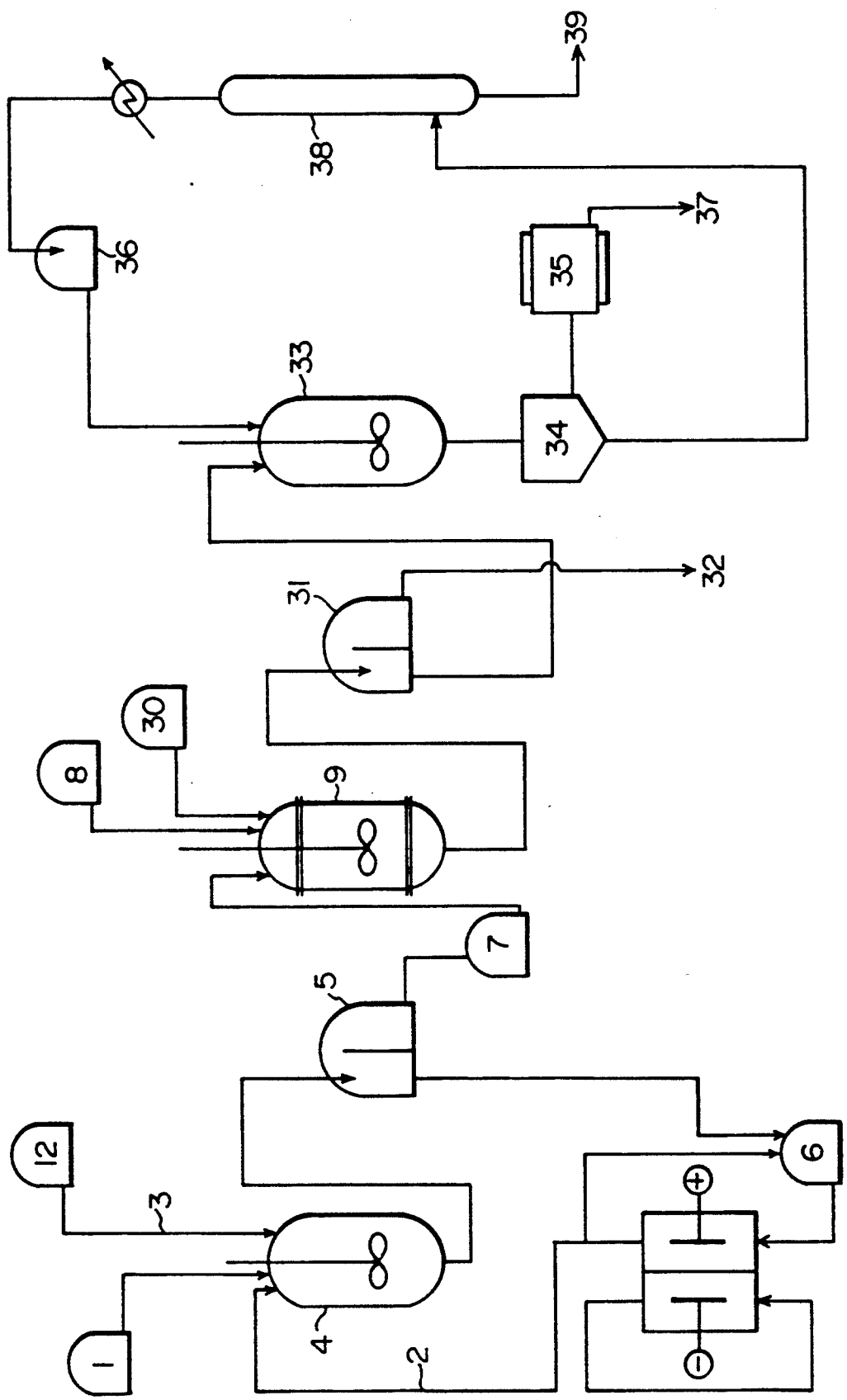

FIG. 2 is a flow sheet chart describing a method to obtain crystals of 2-methyl-1,4-naphthoquinone hydrogensulfite salt.

Steps of from the oxidation reaction of 2-methyl-1,4-naphthoquinone to the Diels-Alder reaction are the same as the 1st step to the 3rd step in the above process in FIG. 1. In FIG. 2, symbols 1 to 9 also show the same apparatuses and lines as in FIG. 1. After completion of the 3rd step, the Diels-Alder reaction vessel 9 contains the reaction mixture comprising 2-methyl-1,4-naphthoquinone, the adduct between 6-methyl-1,4-naphthoquinone and the diene compound, the solvent and the like. An aqueous hydrogensulfite salt solution is added to the Diels-Alder reaction vessel 9 from a tank 30 to extract the 2-methyl-1,4-naphthoquinone as its hydrogensulfite salt into the aqueous phase. The contents are transferred to an oil-water separation vessel 31 and the solvent phase is separated. Then, 2-methyl-1,4-naphthoquinone hydrogensulfite salt in the aqueous phase is deposited by a method such as addition of a recrystallization solvent or salting out and separated, and the crystals are taken out.

In case of adopting addition of a recrystallization solvent, the aqueous phase is supplied to a crystallization vessel 33, a recrystallization solvent is added from a tank 36 to deposit 2-methyl-1,4-naphthoquinone hydrogensulfite salt which is then filtered by a filter 34 and dried by a vacuum dryer 35 to obtain crystals of 2-methyl-1,4-naphthoquinone hydrogen-sulfite salt of a high purity. Examples of preferred recrystallization solvents include alcohols such as methanol, ethanol, propanol and butanol, acetone, etc., and these recrystallization solvents may contain water. The filtrate drawn off from the filter 34 is preferably transferred to a recrystallization solvent recovery tower 38, and the distilled solvent is recovered into the tank 36 and reused. The solvent phase separated in the oil-water separation vessel 31 is taken out through a line 32, and preferably distilled, and the solvent is recovered into the tank 12 and reused.

In case where crystals of 2-methyl-1,4-naphthoquinone hydrogensulfite salt are to be obtained by salting out, after supply of the aqueous phase to the crystallization vessel 33, an inorganic salt such as sodium chloride, sodium sulfite or ammonium sulfate or an organic acid such as citric acid, tartaric acid or oxalic acid or a salt thereof is added, in place of a recrystallization solvent, to the crystallization vessel 33 to deposit 2-methyl-1,4-naphthoquinone hydrogensulfite salt which is then filtered and dried in the same manners as above to obtain crystals of 2-methyl-1,4-naphthoquinone hydrogensulfite salt of a high purity.

A description is given below about the case of obtaining, in the invention, from the accessorily produced 6-substituted-1,4-naphthoquinones a 2-substituted anthraquinone [a 5,8-dihydro-2-substituted anthraquinone represented by the general formula (F) or a 2-substituted-anthraquinone represented by the general formula (G)] useful as a pulp digestion auxiliary or a raw material for synthesis of an anthraquinone derivatives.

After a Diels-Alder reaction is carried out in the same manner as above using a 1,3-butadiene represented by the general formula (D), the resulting 2-substituted-1,4-naphthoquinone is taken out, and on the other hand the mixture containing the Diels-Alder reaction adduct between the 6-substituted-1,4-naphthoquinone and the 1,3-butadiene represented by the general formula (D) is taken out, and the adduct is oxidized to obtain 2-substituted anthraquinones. Although the oxidation method of the adduct is not particularly limited, it is preferred due to ease of handling and an advantage in a cost aspect to use a gas containing molecular oxygen such as air. For instance, after air is blown into the solvent solution, which was obtained after separation of the 2-substituted-1,4-naphthoquinone by recrystallization and contains the Diels-Alder adduct between the 6-substituted-1,4-naphthoquinone and the 1,3-butadiene represented by the general formula (D), to form 2-substituted anthraquinones through oxidation, the 2-substituted anthraquinones are obtained, for example, by concentrating the solution to recrystallize them or by distilling away the solvent and then recrystallize them using another suitable solvent. Alternatively, an aqueous alkali solution is added to the solvent solution containing the adduct to extract the adduct into an aqueous phase, and air is blown thereinto, preferably, at a temperature in the range of 35° to 150° C., whereby the adduct is readily oxidized to obtain a precipitate of the 2-substituted anthraquinones. This method has advantages that the oxidation reaction readily progresses and since almost all the impurities are extracted into the solvent phase purification efficiency is good. The ratio of the obtained 5,8-dihydro-2-substituted-anthraquinone to 2-substituted-anthraquinone can be selected by the oxidation conditions. Although a Diels-Alder reaction adduct between a 6-substituted-1,4-naphthoquinone and a 1,3-butadiene represented by the general formula (D) can also be used as a pulp digestion auxiliary, the adduct is comparatively unstable and is not easy to handle, and thus a 2-substituted anthraquinone is used more preferably.

Figure 3:
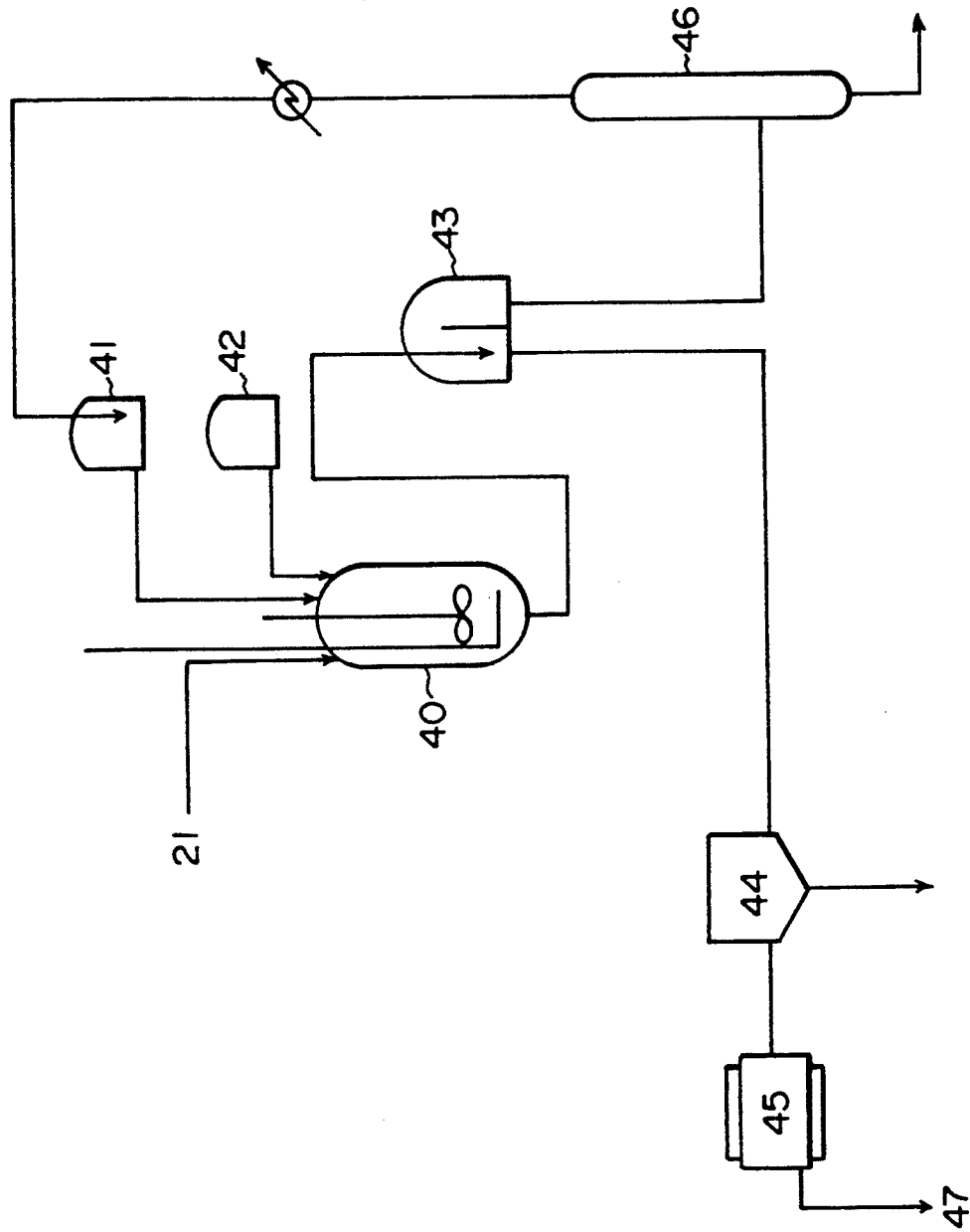

FIG. 3 is a flow sheet chart describing the latter process.

The residue 21 from the tower bottom of the recrystallization solvent recovery tower 18 (FIG. 1) and a solvent from a solvent tank 41 (FIG. 3) are each supplied to an oxidation vessel 40 in FIG. 3. Alternatively, the solvent phase 32 (FIG. 2) after the 2-substituted-1,4-naphthoquinone was extracted as its hydrogensulfite salt into the aqueous phase is supplied to an oxidation vessel 40 in FIG. 3. Then, an aqueous alkali solution is added from an aqueous alkali solution tank 42, and air is blown thereinto with stirring to carry out oxidation. The reaction mixture is supplied to an oil-water separation vessel 43 to separate it into a solvent phase and an aqueous phase containing the 2-substituted anthraquinones, the aqueous phase is supplied to a filter 44 to filter the crystals, and the crystals are dried by a dryer 45 to obtain crystals of the 2-substituted anthraquinones. On the other hand, the solvent phase separated in the oil-water separation vessel 43 is distilled in a solvent recovery tower 46 and the resulting solvent is recovered into the solvent tank 41 and reused.

The invention is detailedly described below according to examples, but it should be noted that the invention in not limited thereto. The following abbreviations are used in expression of the compounds in each of the following tables.

2-MNQ: 2-Methyl-1,4-naphthoquinone
6-MNQ: 6-Methyl-1,4-naphthoquinone
Total MNQ: (2-MNQ)+(6-MNQ)

EXAMPLE 1

50.4 g of 2-Methylnaphthalene and 150 g of o-xylene were charged in a glass reaction vessel equipped with a reflux condenser and a stirring apparatus, the mixture was stirred to dissolve the 2-methylnaphthalene, 6 l of an aqueous sulfuric acid solution of ceric sulfate (containing 600 g of sulfuric acid and 693 g of ceric sulfate) was added, and the mixture was subjected to reaction at 40° C. for 4 hours. After completion of the reaction, the stirring was stopped and the reaction solution was transferred to a separation vessel, where the solvent phase (o-xylene phase) and the aqueous phase were separated. The aqueous phase was extracted with o-xylene and the o-xylene phase was added to the above solvent phase. 1.5 g of Butadiene [butadiene/6-methyl-1,4-naphthoquinone (mole ratio)=1.2] and 30 mg of p-tert-butylcatechol as a polymerization inhibitor were added to part of this solvent phase (containing 11 g of 2-methyl-1,4-naphthoquinone, 4 g of 6-methyl-1,4-naphthoquinone, 1.5 g of unreacted 2-methylnaphthalene and 100 g of o-xylene), and reaction was carried out at 120° C. for 4 hours with stirring in an autoclave. Part of the reaction solution was sampled with every predetermined time, and determination of 2-methyl-1,4-naphthoquinone and 6-methyl-1,4-naphthoquinone was carried out by liquid chromatography to obtain the results in Table 1.

After the reaction, part (60 g) of the reaction mixture was distilled and then dried under reduced pressure. 80 g of Methanol was added to the reaction products after drying, and the liquid temperature was held at 50° C. to dissolve them. The solution was then cooled to 10° C. to carry out crystallization, and the deposited crystals were filtered and dried under reduced pressure to obtain 2-methyl-1,4-naphthoquinone crystals having a purity of 99.5%. On the other hand, the filtrate was distilled to distill away methanol, and the residue was dried under reduced pressure to obtain a butadiene adduct of 6-methyl-1,4-naphthoquinone (1,4,4a,9a-tetrahydro-6-methylanthraquinone) as a solid residue.

EXAMPLE 2

Reactions and analysis were carried out in the same manner as in Example 1 except that part of the solvent phase obtained in Example 1 was used and the temperature of the Diels-Alder reaction was set at 150° C., and the results shown in Table 1 were obtained.

EXAMPLE 3

Reactions and analysis were carried out in the same manner as in Example 1 except that part of the solvent phase obtained in Example 1 was used and the reaction temperature was set at 80° C., and the results shown in Table 1 were obtained.

EXAMPLE 4

Reactions and analysis were carried out in the same manner as in Example 1 except that the concentration of 6-methyl-1,4-naphthoquinone in the solvent phase (o-xylene phase) was adjusted to 1 weight % by decreasing the use amount of the 2-methylnaphthalene oxidation reaction products and the amounts of butadiene and p-tert-butyl catechol used in the Diels-Alder reaction were changed into 0.5 g and 8 mg respectively, and the results shown in Table 1 were obtained.

EXAMPLE 5

Reactions and analysis were carried out in the same manner as in Example 1 except that the concentration of 6-methyl-1,4-naphthoquinone in the solvent phase (o-xylene phase) was adjusted to 8.0 weight % by increasing the use amount of the 2-methylnaphthalene oxidation reaction products and the amounts of butadiene and p-tert-butyl catechol used in the Diels-Alder reaction were changed into 4.0 g and 70 mg respectively, and the results shown in Table 2 were obtained.

EXAMPLE 6

Reactions and analysis were carried out in the same manner as in Example 1 except that the use amount of butadiene was made equal to that of 6-methyl-1,4-naphthoquinone in terms of moles in the Diels-Alder reaction, and the results shown in Table 2 were obtained.

EXAMPLE 7

Reactions and analysis were carried out in the same manner as in Example 1 except that the use amount of butadiene was made to be double the amount of 6-methyl-1,4-naphthoquinone in terms of moles in the Diels-Alder reaction, and the results shown in Table 2 were obtained.

EXAMPLE 8

Reactions and analysis were carried out in the same manner as in Example 1 except that 1.9 g of methyl-butadiene (methybutadiene/6-methyl-1,4-naphthoquinone in mole ratio=1.2) was used in place of 1.5 g of butadiene in the Diels-Alder reaction, and the results shown Table 2 were obtained.

EXAMPLE 9

2-Methylnaphthalene was oxidized with chromic acid in sulfuric acid, and then, 9.0 g of 2-methyl-1,4-naphthoquinone, 6.0 g of 6-methyl-1,4-naphthoquinone and 2.0 g of the unreacted 2-methylnaphthalene were extracted with 100 g of o-xylene. 2.3 g of Butadiene (butadiene/6-methyl-1,4-naphthoquinone by mole ratio=1.2) and 30 mg of p-tert-butyl-catechol as a polymerization inhibitor were added to a solution containing 5.1 weight % the 6-methyl-1,4-naphthoquinone, and the mixture was subjected to reaction with stirring at a temperature of 120° C. for 5 hours in an autoclave. Part of the reaction solution was sampled with every predetermined time and determination of 2-methyl-1,4-naphthoquinone and 6-methyl-1,4-naphthoquinone was carried out to obtain the results shown in Table 3.

EXAMPLE 10

2-Methyl-naphthalene was placed in a glass reaction vessel equipped with a stirrer, a reflux condenser and a hydrogen peroxide dropping apparatus, and 60% aqueous hydrogen peroxide was added dropwise over a period of 2 hours in the presence of a strongly acidic sulfone type ion exchange resin to carry out reaction. The resulting 10 g of 2-methyl-1,4-naphthoquinone, 5 g of 6-methyl-1,4-naphthoquinone and 3.8 g of the unreacted 2-methyl-naphthalene were extracted with 100 g of benzene. To a solution containing this 6-methyl-1,4-naphthoquinone in a concentration of 4.2 weight % were added 2.2 g of butadiene (butadiene/6-methyl-1,4-naphthoquinone by mole ratio=1.2) and 30 mg of p-tert-butyl-catechol as a polymerization inhibitor, and reaction carried out with stirring at 120° C. for 4 hours in an autoclave. Sampling and analysis were carried out in the same manner as in Example 1 to obtain the results shown in Table 3.

EXAMPLE 11

2-Methylnaphthalene was subjected to vapor phase oxidation, and then 8 g of 2-methyl-1,4-naphthoquinone, 7 g of 6-methyl-1,4-naphthoquinone and 1.0 g of the unreacted 2-methylnaphthalene were extracted with 100 g of benzene. To a solution containing this 6-methyl-1,4-naphthoquinone in a concentration of 6.0% were added 3.1 g of butadiene (butadiene/6-methyl-1,4-naphthoquinone by mole ratio=1.2) and 30 mg of p-tert-butyl-catechol as a polymerization inhibitor, and reaction was carried out with stirring at a temperature of 120° C. for 5 hours in an autoclave. The analytical results are shown in Table 3.

TABLE 1

| Reaction time (hr) | Example 1 | | | Example 2 | | | Example 3 | | | Example 4 | | |
|---|---|---|---|---|---|---|---|---|---|---|---|---|
| | 2-MNQ (g) | 6-MNQ (g) | 2-MNQ/Total MNQ weight % | 2-MNQ (g) | 6-MNQ (g) | 2-MNQ/Total MNQ weight % | 2-MNQ (g) | 6-MNQ (g) | 2-MNQ/Total MNQ weight % | 2-MNQ (g) | 6-MNQ (g) | 2-MNQ/Total MNQ weight % |
| 0 | 11.0 | 4.0 | 73.3 | 11.0 | 4.0 | 73.3 | 11.0 | 4.0 | 73.3 | 2.8 | 1.1 | 71.8 |
| 0.5 | | | | 10.6 | 1.3 | 89.1 | | | | | | |
| 1.0 | 10.8 | 1.7 | 86.4 | 10.3 | 0.5 | 95.4 | | | | | | |
| 1.5 | | | | 10.1 | 0.2 | 98.1 | | | | | | |
| 2.0 | 10.9 | 1.1 | 90.8 | | | | 11.0 | 1.9 | 85.3 | 2.9 | 0.6 | 82.9 |
| 3.0 | 11.1 | 0.4 | 96.5 | | | | | | | | | |
| 4.0 | 11.0 | 0.1 | 99.1 | | | | 11.2 | 1.5 | 88.2 | 2.7 | 0.4 | 87.1 |
| 8.0 | | | | | | | 10.9 | 0.7 | 94.0 | 2.8 | 0.2 | 93.3 |

TABLE 1-continued

| Reaction time (hr) | Example 1 | | | Example 2 | | | Example 3 | | | Example 4 | | |
|---|---|---|---|---|---|---|---|---|---|---|---|---|
| | 2-MNQ (g) | 6-MNQ (g) | 2-MNQ/Total MNQ weight % | 2-MNQ (g) | 6-MNQ (g) | 2-MNQ/Total MNQ weight % | 2-MNQ (g) | 6-MNQ (g) | 2-MNQ/Total MNQ weight % | 2-MNQ (g) | 6-MNQ (g) | 2-MNQ/Total MNQ weight % |
| 10.0 | | | | | | | 11.1 | 0.5 | 95.7 | 2.8 | 0.1 | 96.6 |

TABLE 2

| Reaction time (hr) | Example 5 | | | Example 6 | | | Example 7 | | | Example 8 | | |
|---|---|---|---|---|---|---|---|---|---|---|---|---|
| | 2-MNQ (g) | 6-MNQ (g) | 2-MNQ/Total MNQ weight % | 2-MNQ (g) | 6-MNQ (g) | 2-MNQ/Total MNQ weight % | 2-MNQ (g) | 6-MNQ (g) | 2-MNQ/Total MNQ weight % | 2-MNQ (g) | 6-MNQ (g) | 2-MNQ/Total MNQ weight % |
| 0 | 25.5 | 9.4 | 73.1 | 11.0 | 4.0 | 73.3 | 11.0 | 4.0 | 73.3 | 11.0 | 4.0 | 73.3 |
| 0.5 | 25.3 | 4.5 | 84.9 | | | | 10.7 | 1.6 | 87.0 | | | |
| 1.0 | 25.2 | 2.2 | 92.0 | | | | 11.1 | 0.8 | 93.3 | 10.7 | 1.4 | 88.5 |
| 1.5 | 25.6 | 1.1 | 95.9 | | | | 11.3 | 0.4 | 96.6 | | | |
| 2.0 | 25.4 | 0.6 | 97.7 | 11.2 | 2.0 | 84.8 | 11.1 | 0.2 | 98.2 | 10.9 | 0.6 | 94.8 |
| 3.0 | | | | | | | | | | 11.1 | 0.2 | 98.2 |
| 4.0 | | | | 11.1 | 0.8 | 93.3 | | | | | | |
| 8.0 | | | | 10.8 | 0.3 | 97.3 | | | | | | |
| 10.0 | | | | 10.9 | 0.2 | 98.2 | | | | | | |

TABLE 3

| Reaction time (hr) | Example 9 | | | Example 10 | | | Example 11 | | |
|---|---|---|---|---|---|---|---|---|---|
| | 2-MNQ (g) | 6-MNQ (g) | 2-MNQ/Total MNQ weight % | 2-MNQ (g) | 6-MNQ (g) | 2-MNQ/Total MNQ weight % | 2-MNQ (g) | 6-MNQ (g) | 2-MNQ/Total MNQ weight % |
| 0 | 9.0 | 6.0 | 60.0 | 10.0 | 5.0 | 66.7 | 8.0 | 7.0 | 53.3 |
| 1.0 | 9.0 | 3.3 | 73.2 | 10.1 | 2.9 | 77.7 | 7.9 | 3.7 | 68.1 |
| 2.0 | 9.1 | 1.4 | 86.7 | 10.2 | 1.5 | 87.2 | 7.8 | 2.0 | 79.6 |
| 3.0 | 8.8 | 0.8 | 92.0 | 9.9 | 0.8 | 92.5 | 8.1 | 1.2 | 87.1 |
| 4.0 | 8.9 | 0.5 | 95.0 | 9.8 | 0.4 | 96.1 | 7.9 | 0.7 | 91.9 |
| 5.0 | 9.2 | 0.1 | 98.5 | 10.1 | 0.2 | 98.1 | 8.2 | 0.4 | 95.3 |

EXAMPLE 12

(The 1st step)

196 kg of concentrated sulfuric acid and 464.8 kg of ceric sulfate $Ce(SO_4)_2$ were dissolved in 1.5 m$^3$ of distilled water, and distilled water was added to make the volume 2 m$^3$. The aqueous solution was placed in a glass-lined reaction vessel equipped with a reflux condenser and an agitation apparatus, and held at 50° C. 20 kg of 2-Methylnaphthalene and 70 kg of o-xylene were added thereto, and the mixture was subjected to an oxidation reaction for 3 hours with stirring.

The 2nd step

After completion of the oxidation reaction, the reaction products were transferred to a separation vessel to separate them into a solvent phase (o-xylene phase) and an aqueous phase, and the aqueous phase was extracted three times with 15 kg of o-xylene.

The 3rd step

The solvent phase and the extraction solvent phase respectively after separation were mixed and poured into a Diels-Alder reaction vessel, 6.3 kg of butadiene was added, and reaction was carried out with stirring at a temperature of 120° C. for 4 hours.

The 4th step

The reaction mixture was distilled and the solvent and the unreacted 2-methylnaphthalene were recovered. The remaining reaction products were then dried under reduced pressure.

The 5th step

The dried reaction products were placed in a crystallizing reaction vessel, 170 kg of methanol was added, and the mixture was held at 50° C. to completely dissolve them. Then, the mixture was cooled to 10° C. to carry out crystallization, and the deposited crystals were separated by a filter and dried under reduced pressure to obtain 11.9 kg of 2-methyl-1,4-naphthoquinone (mole yield based on the charged 2-methylnaphthalene : 49.1%). It's purity was 99.5%. On the other hand, by distilling the filtrate to recover methanol, a butadiene adduct of 6-methyl-1,4-naphthoquinone (1,4,4a,9a-tetrahydro-6-methylanthraquinone) remained as a solid residue.

EXAMPLE 13

To the solid residue consisting of the butadiene adduct of 6-methyl-1,4-naphthoquinone obtained in the 5th step of Example 12 were added a 1N aqueous sodium hydroxide solution and o-xylene, and after 30 minutes stirring air was blown thereinto at 50° C. for 2 hours. By subsequent allowing to stand, the mixture was separated into an oil phase and an aqueous phase containing precipitate. The aqueous phase was separated and filtered, and the obtained precipitate was dried under reduced pressure to obtain 5 kg of 2-methylanthraquinones (a mixture of 5,8-dihydro-2-methylanthraquinone and methylanthraquinone). The mole yield based on the charged 2-methylnaphthalene was 16.0%.

EXAMPLE 14

The 1st to 3rd steps of Example 12 were reconducted. To the reaction solution obtained in the 3rd step was added 37.5 kg of a 33 weight % aqueous sodium hydrogensulfite solution, and the mixture was subjected to reaction at 50° C. for 3 hours. Thereafter, by allowing the reaction mixture to stand, the mixture was separated into an oil phase and an aqueous phase (an aqueous solution of 2-methyl-1,4-naphthoquinone sodium hydrogen-sulfite). The aqueous phase was separated and, after addition of 120 kg of isopropanol, stirred at 25° C. for 2 hours, and the deposited crystals were filtered and dried under reduced pressure at 50° C. to obtain 19.7 kg of 2-methyl-1,4-naphthoquinone sodium hydrogensulfite.

EXAMPLE 15

A 0.5N aqueous sodium hydroxide solution was added to the oil phase obtained in Example 14, and, after 30 minutes stirring, air was blown thereinto at 70° C. for 2 hours. Then, the oil phase and the aqueous phase containing the precipitate were separated, and the aqueous phase was dried under reduced pressure to obtain 5.5 kg of 2-methylanthraquinone.

EXAMPLE 16

The 1st to 3rd steps of Example 12 were reconducted. 37.5 kg of the 33 weight % aqueous sodium hydrogensulfite solution was added to the reaction solution obtained in the 3rd step, followed by reaction at 50° C. for 3 hours. The reaction mixture was then allowed to stand to separate it into an oil phase and an aqueous phase (an aqueous solution of 2-methyl-1,4-naphthoquinone sodium hydrogensulfite). The aqueous phase was separated and, after addition of 4 kg of sodium chloride, stirred at 20° C. for 1 hour, and the deposited crystals were filtered and dried under reduced pressure at 50° C. to obtain 20.5 kg of sodium salt of 2-methyl-1,4-naphthoquinone hydrogensulfite.

EXAMPLE 17

2-Ethylnaphthalene dissolved in o-xylene and an aqueous sulfuric acid solution of ceric sulfate were poured into a reaction vessel equipped with a reflux condenser and a stirring apparatus, and the mixture was subjected to reaction with stirring at 50° C. for 90 minutes. After completion of the reaction, the stirring was stopped, the reaction solution was transferred to a separation vessel to separate it into a solvent phase (o-xylene phase) and an aqueous phase. The aqueous phase was extracted with o-xylene, and the o-xylene phase was added to the above solvent phase. To part (containing 8 g of 2-ethyl-1,4-naphthoquinone, 5 g of 6-ethyl-1,4-naphthoquinone, 1.5 g of the unreacted 2-ethylnaphthalene and 100 g of o-xylene) of this solvent phase were added 1.9 g of butadiene (butadiene/6-ethyl-1,4-napthoquinone by mole ratio=1.3) and 30 mg of p-tert-butyl-catechol as a polymerization inhibitor, and reaction was carried out with stirring at a reaction temperature of 110° C. for 5 hours in an autoclave. After the reaction, part of the reaction mixture was distilled and then dried under reduced pressure. 100 g of Methanol was added to the reaction products after drying, the mixture was stirred at 50° C. and cooled, and the deposited crystals were filtered, washed with pure water and dried under reduced pressure to obtain 2-ethyl-1,4-naphthoquinone having a purity of 99.2%. Then, the filtrate was distilled to recover methanol, and to the solid residue mainly consisting of the adduct of 6-ethyl-1,4-naphthoquinone (1,4,4a,9a-tetrahydro-6-ethylanthraquinone) were added a 0.5N aqueous sodium hydroxide solution and o-xylene, and after 30 minutes stirring air was blown thereinto at 60° C. for 3 hours. The aqueous phase containing the precipitate obtained by allowing to stand was filtered, and the filter cake was washed with pure water and dried under reduced pressure to obtain 5.4 g of 2-ethylanthraquinone.

EXAMPLE 18

2-t-Amylnaphthalene dissolved in o-xylene and an aqueous sulfuric acid solution of ceric sulfate were poured into a glass reaction vessel equipped with a reflux condenser and a stirring apparatus, followed by reaction with stirring at 50° C. for 2 hours. After completion of the reaction, the stirring was stopped, and the reaction solution was transferred to a separation vessel, where the solvent phase (o-xylene phase) and the aqueous phase were separated. The aqueous phase was extracted with o-xylene and the o-xylene phase was added to the previous solvent phase. To part (containing 4.2 g of 2-t-amyl-1,4-naphthoquinone, 3.1 g of 6-t-amyl-1,4-naphthoquinone, 2.0 g of the unreacted 2-t-amylnaphalene and 80 g of o-xylene) of this solvent phase were added 0.95 g of butadiene and 15 mg of p-tert-butyl-catechol as a polymerization inhibitor, and reaction was carried out with stirring at a reaction temperature of 110° C. for 5 hours. After the reaction, part of the reaction mixture was distilled and then dried under reduced pressure. 100 g of methanol was added to the reaction products after drying, the mixture was stirred at 50° C. and cooled, and the deposited crystals were filtered, washed with pure water and dried under reduced pressure to obtain 2-t-amyl-1,4-naphthoquinone having a purity of 99.1%. Then, the filtrate was distilled to recover methanol, and to the solid residue manly consisting of the adduct of 6-t-amyl-1,4-naphthoquinone (1,4,4a,9a-tetrahydro-6-t-amylanthraquinone) were added a 0.5N aqueous sodium hydroxide solution and o-xylene, and after 30 minutes stirring air was blown thereinto at 80° C. for 3 hours. The aqueous phase containing the precipitate obtained by allowing to stand was filtered, and the obtained precipitate was washed with pure water and dried under reduced pressure to obtain 3 g of 2-t-amylanthraquinone.

EXAMPLE 19

A nitric acid solution of ceric ammonium nitrate (ceric ion concentration is 0.5 mol/l and nitric acid concentration is 2.0 mol/l) was placed in a glass vessel equipped with a reflux condenser and a stirring apparatus, and held at 70° C. 2-Nitronaphthalene was added thereto, followed by reaction with stirring for 2 hours. After the reaction, and the solution was cooled to deposit crystals, which was then collected by filtration and washed with pure water to obtain crystals comprising 10 g of 2-nitro-1,4-naphthoquinone and 18 g of 6-nitro-1,4-naphthoquinone. The crystals were admixed with 150 cc of ethylene glycol monomethyl ether, and the resulting mixture and 8 g of 1,3-butadiene were placed in an autoclave equipped with a stirring apparatus, and subjected to reaction with stirring at 70° C. for 6 hours. After the reaction, the solution was cooled and filtered, and the resulting crystals were washed with pure water and methanol and dried under reduced pressure to obtain 7 g of 2-nitro-1,4-naphthoquinone having a purity of 99%. Then, a 0.5N aqueous sodium hydroxide solution was added to the filtrate, and after 15 minutes stirring air was blown thereinto at 70° C. for 4 hours, and the resulting slurry was filtered to obtain 17 g of 2-nitroanthraquinone.

EXAMPLE 20

2-Carboxynaphthalene dissolved in o-xylene and an aqueous sulfuric acid solution of ceric sulfate were poured into a glass reaction vessel equipped with a reflux condenser and a stirring apparatus, and reacted with stirring at 60° C. for 2.5 hours. After completion of the reaction, stirring was stopped, and the reaction solution was transferred to a separation vessel, where the solvent phase (o-xylene phase) and the aqueous phase were separated. To part (containing 7.2 g of 2-carboxy-1,4-naphthoquinone, 5.3 g of 6-carboxy-1,4-naphthoquinone, 2.6 g of the unreacted 2-carboxynaphthalene and 100 g of o-xylene) of this solvent phase were added 1.9 g of butadiene and 30 mg of p-tert-butylcatechol as a polymerization inhibitor, and the mixture was subjected to reaction with stirring at 110° C. for 5 hours in an autoclave. After the reaction, part of the reaction mixture was distilled and then dried under reduced pressure. 100 g of Methanol was added to the reaction products after drying, and after stirring at 50° C. the mixture was cooled, and the deposited crystals were filtered, washed with pure water and dried under reduced pressure to obtain 2-carboxy-1,4-naphthoquinone having a purity of 98.5%. Then, the filtrate was distilled to recover methanol, a 0.5N aqueous sodium hydroxide solution and o-xylene were added to the solid residue consisting mainly of the adduct of 6-carboxy-1,4-naphthoquinone (1,4,4a,9a-tetrahydro-6-carboxyanthraquinone), and after 30 minutes stirring air was blown thereinto at 80° C. for 3 hours. The aqueous phase containing the precipitate obtained by allowing to stand was filtered, and the obtained precipitate was washed with pure water and dried under reduced pressure to obtain 5 g of 2-carboxyanthraquinone.

EXAMPLE 21

2-Chloronaphthalene dissolved in o-xylene and an aqueous sulfuric acid solution of ceric sulfate were poured into a glass reaction vessel equipped with a reflux condenser and a stirring apparatus, and subjected to reaction at 60° C. for 90 minutes with stirring. After completion of the reaction, stirring was stopped, the reaction solution was transferred to a separation vessel, and the solvent phase (o-xylene phase) and the aqueous phase were separated. The aqueous phase was extracted with o-xylene, and the o-xylene phase was added to the above solvent phase. To part (containing 4 g of 2-chloro-1,4-naphthoquinone, 5 g of 6-chloro-1,4-naphthoquinone, 2.2 g of the unreacted 2-chloronaphthalene and 100 g of o-xylene) of this solvent phase were added 1.9 g of butadiene and 30 mg of p-tert-butyl-catechol, and reaction was carried out at a reaction temperature of 110° C. for 5 hours with stirring in an autoclave. After the reaction, part of the reaction mixture was distilled and then dried under reduced pressure. 100 g of Methanol was added to the reaction products after drying, and after stirring at 50° C. the mixture was cooled, and the deposited crystals were filtered, washed with pure water and dried under reduced pressure to obtain 2-chloro-1,4-naphthoquinone having a purity of 98.7%. Then, the filtrate was distilled to recover methanol, and to the solid residue consisting mainly of the adduct of 6-chloro-1,4-naphthoquinone (1,4,4a,9a-tetrahydro-6-chloroanthraquinone) were added a 0.5N aqueous sodium hydroxide solution and o-xylene, and after 30 minutes stirring air was blown thereinto at 80° C. for 3 hours. The aqueous phase containing the precipitate obtained by allowing to stand was filtered, and the filter cake was washed with pure water and dried under reduced pressure to obtain 5.1 g of 2-chloroanthraquinone.

EXAMPLE 22

19 g of 2-Methyl-naphalene containing 10 weight % 1-methyl-naphthalene and 50 g of o-xylene were charged in a glass reaction vessel equipped with a reflux condenser and a stirring apparatus, and stirred to form a solution, an aqueous sulfuric acid solution of ceric sulfate was poured therein, and the mixture was subjected to reaction at 40° C. for 4 hours with stirring. After completion of the reaction, stirring was stopped and the reaction solution was transferred to a separation vessel, where the solvent phase (o-xylene phase) and the aqueous phase were separated. The aqueous phase was extracted with o-xylene, and the o-xylene phase was added to the previous solvent phase. To this solvent phase (containing 11 g of 2-methyl-1,4-naphthoquinone, 4 g of 6-methyl-1,4-naphthoquinone, 0.5 g of 5-methyl-1,4-naphthoquinone, 0.2 g of 1,4-naphthoquinone, 1.7 g of the unreacted 2-methyl-naphthalene, 0.8 g of 1-methyl-naphthalene and 100 g of o-xylene) were added 1.8 g of butadiene and 30 mg of p-tert-butyl-catechol as a polymerization inhibitor, and the mixture was subjected to reaction at a reaction temperature of 120° C. for 4 hours with stirring in an autoclave. After the reaction, part (60 g) of the reaction mixture was distilled and then dried under reduced pressure. 80 g of Methanol was added to the reaction products after drying, followed by stirring at 50° C. to dissolve them. Then, the solution was cooled to 10° C., and the deposited crystals were filtered, washed with pure water and dried under reduced pressure to obtain 2-methyl-1,4-naphthoquinone having a purity of 99.1%.

As is seen from the foregoing, according to the invention separation between 2-substituted-1,4-naphthoquinone and 6-substituted-1,4-naphthoquinone, which has been difficult due to very much resemblance in physical properties can efficiently be carried out, and thereby the 2-substituted-1,4-naphthoquinone having a high purity can be obtained. Further, since 2-substituted anthraquinones, which are useful as a pulp digestion auxiliary or a raw material for synthesis of anthraquinone derivatives, can be obtained as a by-product according to the invention, it is possible to effectively utilize a raw material 2-substituted naphthalene, lower preparation cost and decrease organic wastes by a large margin. According to the invention it is further possible to prepare a 2-substituted-1,4-naphthoquinone safely without using usual chromic acid which has a danger of contaminating the human body and environment.

We claim:

1. A process for preparation of a 2-substituted-1,4-naphthoquinone which comprises oxidizing a 2-substituted naphthalene to obtain reaction products comprising a 2-substituted-1,4-naphthoquinone and a 6-substituted-1,4-naphthoquinone; adding a diene compound to the reaction products and heating the mixture to a temperature of from 50° to 200° C. to form a Diels- Alder reaction adduct between the diene compound and the 6-substituted-1,4-naphthoquinone in the reaction products; and separating the 2-substituted-1,4-naphthoquinone from the adduct.

2. The process of claim 1 wherein the 2-substituted naphthalene is a 2-substituted naphthalene represented by the general formula (A):

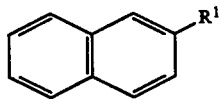

(wherein $R^1$ is an alkyl group having 1 to 5 carbon atoms, a nitro group, a carboxyl group or a halogen atom), and the diene compound is a diene compound represented by the general formula (D)

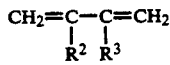

(wherein $R^2$ and $R^3$ are each independently a hydrogen atom, a methyl group or an ethyl group).

3. A process for preparation of a 2-substituted-1,4-naphthoquinone which comprises the following steps, step (1) oxidizing a 2-substituted naphthalene with an acidic aqueous solution of a ceric salt; step (2) extracting the reaction products obtained by the oxidation reaction of step (1) and comprising 2-substituted-1,4-naphthoquinone and 6-substituted-1,4-naphthoquinone with a solvent, and separating the solvent phase from the phase of the acidic aqueous solution of the ceric salt; step (3) adding a diene compound to the solvent phase containing the reaction products separated in step (2) and heating the mixture to a temperature of from 50° to 200° C. to form a Diels-Alder reaction adduct between the diene compound and the 6-substituted-1,4-naphthoquinone; step (4) separating and recovering the solvent from the reaction mixture obtained in step (3); and step (5) removing the Diels-Alder reaction adduct from the reaction mixture after separation of the solvent to obtain the 2-substituted-1,4-naphthoquinone having a high purity.

4. A process for preparation of 2-methyl-1,4-naphthoquinone hydrogensulfite salt which comprises oxidizing 2-methylnaphthalene to obtain reaction products comprising 2-methyl-1,4-naphthoquinone and 6-methyl-1,4-naphthoquinone; adding a diene compound to the reaction products and heating the mixture to a temperature of from 50° to 200° C. to form a Diels-Alder reaction adduct between the diene compound and the 6-methyl-1,4-naphthoquinone in the reaction products; and adding an aqueous hydrogensulfite salt solution to the resulting reaction mixture to extract the 2-methyl-1,4-naphthoquinone into the aqueous phase as its hydrogen-sulfite salt.

5. A process for preparation of a -b 5,8-dihydro-2-substituted-anthraquinone and/or a 2-substituted-anthraquinone which comprises oxidizing a 2-substituted naphthalene to obtain reaction products comprising a 2-substituted-1,4-naphthoquinone and a 6-substituted-1,4-naphthoquinone; adding a 1,3-butadiene to the reaction products and heating the mixture at a temperature of from 50° to 200° C. to form a Diels-Alder reaction adduct between the 1,3-butadiene and the 6-substituted-1,4-naphthoquinone in the reaction products; separating the 2-substituted-1,4-naphthoquinone from the adduct, and oxidizing the adduct.

6. The process of any one of claims 1 to 5 wherein the Diels-Alder reaction is carried out in the range of 80° to 150° C.

7. The process of claim 1, wherein from about 1 to 2 moles of the diene compound are used per mole of the 6-substituted-1,4-naphthoquinone.

8. The process of claim 1, wherein in the Diels-Alder reaction a solvent is used in which the 6-substituted-1,4-naphthoquinone and the diene compound have a large solubility and the concentration of the 6-substituted-1,4-naphthoquinone is from about 0.5 to 15 weight percent in the solvent.

9. The process of any one of claims 1 to 5 wherein the Diels-Alder reaction is carried out in the presence of a polymerization inhibitor.

10. A method of recovering high purity 2-substituted-1,4-naphthoquinone from a mixture of 2-substituted-1,4-naphthoquinone and 6-substituted-1,4-naphthoquinone which comprises adding a 1,3-butadiene compound to the mixture, heating the mixture to a temperature of from 50° to 200° C. to form a Diels-Alder adduct between the 1,3-butadiene compound and the 6-substituted-1,4-naphthoquinone in the mixture; and separating the 2-substituted-1,4-naphthoquinone from the adduct in the mixture.

11. The method of claim 10 wherein the Diels-Alder reaction is carried out in the presence of a solvent in which the 6-substituted-1,4-naphthoquinone and the 1,3-butadiene compound are soluble and wherein the concentration of the 6-substituted-1,4-naphthoquinone in the solvent is from 0.5 to 15 weight percent.

12. The method of claim 10 or 11 wherein the substituent at the 2-position of the 2-substituted-1,4-naphthoquinone is an alkyl group having 1 to 5 carbon atoms, a nitro group, a carboxyl group or a halogen atom.

13. The method of claim 12 wherein from about 1.0 to about 2.0 moles of the 1,3-butadiene compound per mole of the 6-substituted-1,4-naphthoquinone is added to the mixture.

* * * * *